Dec. 11, 1956 G. MERRILL Plant Pat. 1,538
PEACH TREE
Filed Dec. 6, 1955
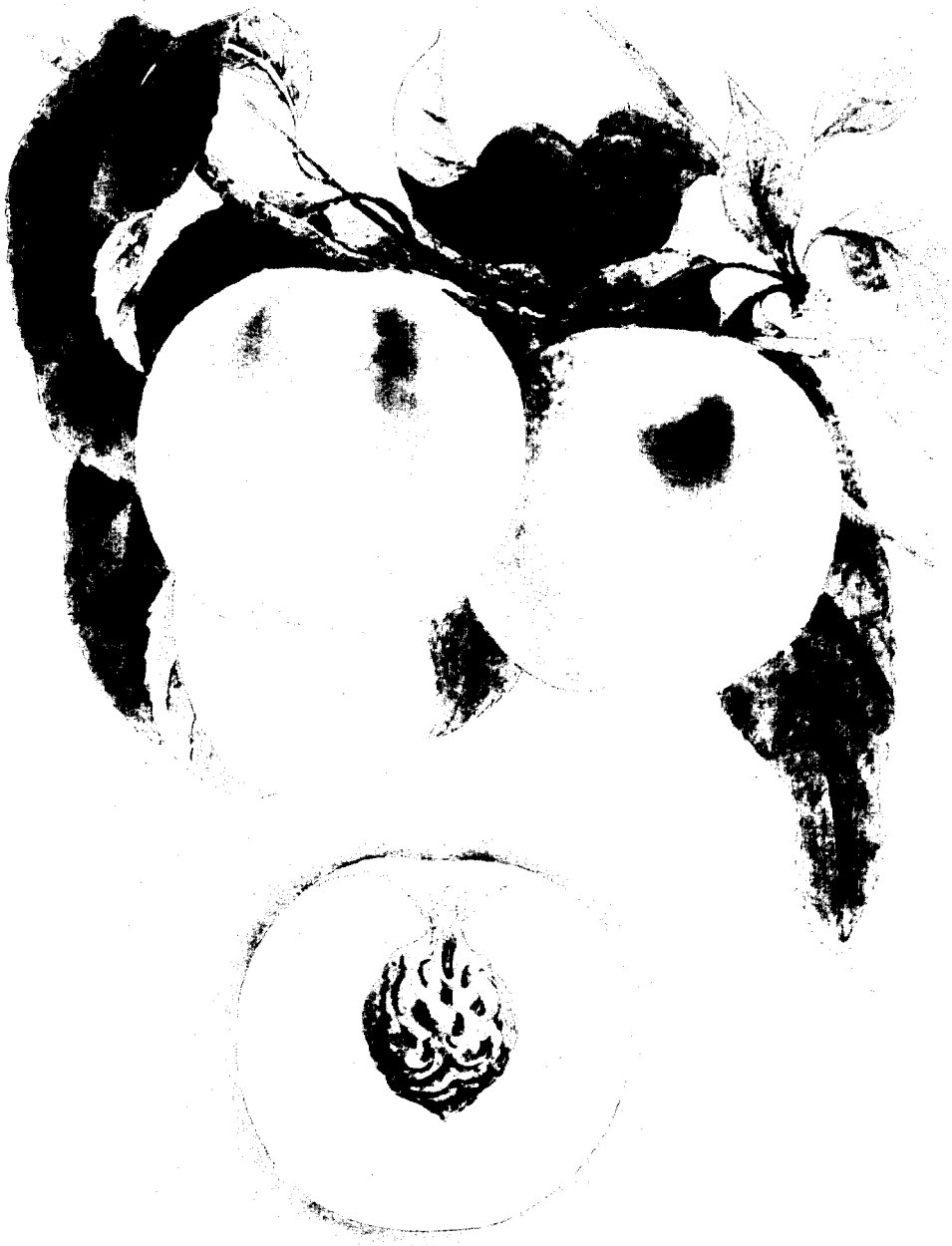
WITNESS
Addison E. Avery
INVENTOR
Gruen Merrill United States Patent Office Plant Pat. 1,538
Patented Dec. 11, 1956

1,538

PEACH TREE

Grant Merrill, Red Bluff, Calif.

Application December 6, 1955, Serial No. 551,464

1 Claim. (Cl. 47—62)

This invention relates to a new and distinct variety of peach tree which bears large, yellow fleshed, firm, freestone fruit, with extensive red blush and which is commercially desirable, especially by reason of its ripening period relative to other varieties of fruit.

A distinguishing character of the present variety of fruit is that it starts its ripening about the time July Elberta (United States Plant Patent Number 15) finishes its ripening season and completes its ripening about the time the variety J. H. Hale (unpatented) starts to ripen.

The fruit of the present variety is distinguished from other fruit ripening at this season by its larger size, higher color and greater firmness.

In comparison to J. H. Hale (unpatented) the instant variety ripens about ten (10) days earlier, is approximately as firm, has a little more red blush, does not have as many split pits and the blossoms do not require cross-pollination in order to set fruit.

I originated the present variety of peach tree on my farm near Red Bluff, Tehama County, California, in the following manner:

In 1945 seeds from peach trees in my variety breeding plot were planted. All of these were open pollinated seedlings of crosses in which J. H. Hale (unpatented) or Candoka (United States Plant Patent Number 51) had been used, except for one row which were seeds from open pollinated Kirkman Gem (United States Plant Patent Number 506).

In 1949 it was observed that in the row in which Kirkman Gem (United States Plant Patent Number 506) seedlings were planted, there was one seedling, the first seedling in the row, which was very much different from any of the other seedlings. Because of this, it is assumed that there was an error and that this first seedling, which more nearly resembled J. H. Hale (unpatented) was from one of the seedlings of the J. H. Hale (unpatented) seedlings in the Test Plot.

This seedling appeared promising because of its great firmness, large size and relatively high color and because it ripened in the season between July Elberta (United States Plant Patent Number 15) and J. H. Hale (unpatented). In February, 1951, scions from this tree were grafted onto ten (10) trees in an old Golden Jubilee (unpatented) block. These asexual reproductions were found to carry forward each and every characteristic of the parent seedling.

In 1951, budwood of this variety was sent to Washington State where the variety was budded onto young peach trees in the Grandview area of Washington. When this variety came into bearing it appeared especially highly colored, especially firm and well adapted to that area, having more red blush than J. H. Hale grown in the same area.

In the drawings the fruit is shown in elevation together with twigs and leaves and also sectional elevation of fruit with the stone exposed.

Referring now more specifically to the pomological details of this new and distinct variety of peach tree, the following is an outline description thereof; all major color plate identifications being by reference to Maerz and Paul Dictionary of Color:

Tree:
- *Size.*—Medium.
- *Vigor.*—Medium vigorous.
- *Growth.*—Medium upright.
- *Density.*—Medium dense.
- *Shape.*—Normally pruned to vase form.
- *Production.*—Productive.
- *Bearing.*—Regular bearer.

Trunk:
- *Size.*—Medium stocky.
- *Surface.*—Medium shaggy.

Branches:
- *Size.*—Medium stocky.
- *Surface.*—Medium shaggy.
- *Color.*—Brown to grayish brown.
- *Lenticels.*—Medium quantity.

Leaves:
- *Size.*—Medium. Length 4″ to 6½″. Average 5½″. Width 1″ to 2″. Average 1⅝″.
- *Form.*—Lanceolate; tip acuminate; medium thin.
- *Surface.*—Smooth, except along midrib, which is moderately rugose.
- *Margin.*—Crenate.
- *Petiole.*—Medium long; medium thick.
- *Glands.*—One to seven, mostly two to four. Alternate; medium size; reniform; green. On lower part of leaf and upper part of petiole.
- *Stipules.*—On new growth falling off early.
- *Color.*—Top side—medium green (23–L–4). Under side—lighter green (22–I–5). Heavy midrib on under side yellowish green (19–K–1).

Flower buds:
- *Size.*—Medium.
- *Length.*—Medium.
- *Form.*—Plump; round; free.
- *Pubescence.*—Pubescent.

Flowers:
- *Blooming period.*—Latter part of mid-season as compared to other varieties.
- *Date of first bloom.*—March 9, 1955.
- *Date of full bloom.*—March 21, 1955.
- *Size.*—Small.
- *Pollen.*—Present.
- *Color.*—Pink with slight salmon tinge.

Fruit:
- *Maturity when described.*—Firm ripe, but the soft ripe description is given when significantly different from the firm ripe description.
- *Date of first picking.*—July 20, 1955.
- *Date of last picking.*—August 1, 1955.
- *Size.*—Variable; large. Axial diameter mostly 2⅝″ to 2¾″, many larger. Transverse and suture plane mostly 2¾″ to 3⅛″, many larger. Average cheek to cheek 2½″ to 3⅛″, many larger.
- *Form.*—Globose to slightly flattened at stem end in larger sizes, some oblong in the smaller sizes.
- *Suture.*—Distinct but shallow. Extends from base, but discontinuous at apex with slight depression beyond pistil point.
- *Ventral surface.*—Slightly lipped on some fruit throughout. Lips usually equal, sometimes unequal.
- *Cavity.*—Abrupt. Elongated in suture plane with suture showing on both sides. Average depth—½″. Average breadth—⅝″ to ¾″. Markings—none on some, others show some red blush.

*Base.*—Retuse.
*Apex.*—Rounded to retuse.
*Pistil point.*—Apical.

Skin:
*Thickness.*—Medium.
*Texture.*—Medium tender. Tenacious to flesh when firm ripe. Free when soft ripe.
*Tendency to crack.*—None.
*Down.*—Scant; short.
*Color.*—Bright yellow under-color (9–K–5) shading to (9–K–7), to as dark as (11–G–9). Red blush covering one quarter to one half the surface of the peach, occasionally more, grading from a light red (3–L–1) to dark red (6–L–5).

Flesh:
*Color of flesh.*—Light yellow near stem end (9–L–5) grading to darker yellow at the apex (9–L–8), mottled with red next to the stone grading from intense red next to the pit (4–L–6), to a lighter red (1–K–10) and reaching a light red (1–J–10) midway between the stone and the skin.
*Surface of pit cavity.*—Yellow, mottled red, becoming completely red when soft ripe.
*Fibers.*—Few.
*Amygdalin.*—Moderate.
*Texture.*—Very firm to melting when soft ripe.
*Ripens.*—Evenly.
*Flavor.*—Mild sub-acid.
*Aroma.*—Average or medium.
*Eating quality.*—Good.

Stone:
*Type.*—Free.
*Adherence to flesh.*—Usually adheres to flesh slightly along both dorsal and ventral edges at the stem end when firm ripe. Completely free when soft ripe.
*Size.*—Large. Length mostly 1½". Breadth mostly 1⅛" to 1¼". Thickness mostly ¾".

*Form.*—Mostly obovate.
*Base.*—Straight to slightly oblique.
*Hilum.*—Oval.
*Apex.*—Cuspidate.
*Sides.*—Usually nearly equal.
*Surface.*—Irregularly furrowed toward apex, pitted toward base.
*Ridges.*—Ridges rounded toward base and middle.
*Pits.*—Circular.
*Ventral edge.*—Without wing toward base.
*Dorsal edge.*—Full with deep groove toward base.
*Tendency to split.*—Slight except in very large peaches.
*Color.*—Reddish purple (6–K–5) grading to (7–L–12).

Use: Long distance shipping; local market; dessert; culinary; canning.
Keeping quality: Good.
Shipping quality: Good.

The tree and its fruit herein described may vary some due to climatic and soil conditions under which the variety may be grown, and the method of growing, including fertilizing, pruning, thinning, the pests and diseases present on the tree, and other causes.

The following is claimed:

A new and distinct variety of peach tree substantially as herein illustrated and described, characterized as to novelty by ripening during the period between July Elberta and J. H. Hale, the fruit resembling J. H. Hale in its large size and firm flesh, but being an improvement thereover by ripening usually about ten days earlier, and having more red color, being self-fertile, and by not having as many split pits.

No references cited.